June 10, 1969 H. A. JOHNSON, JR., ET AL Plant Pat. 2,892
STRAWBERRY PLANT
Filed July 10, 1967
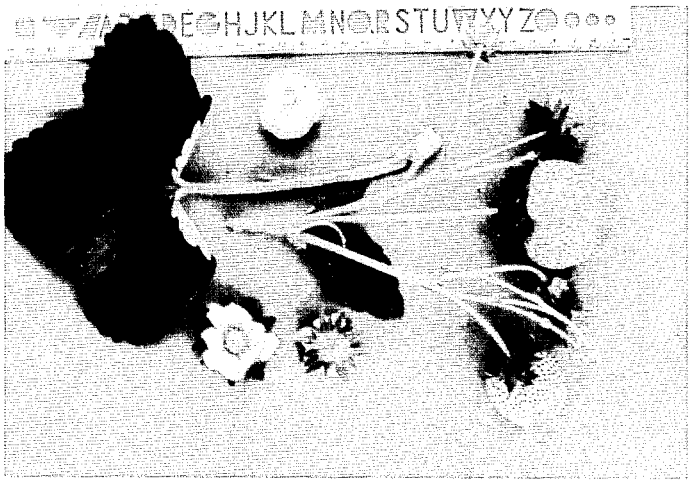
INVENTORS:
HAROLD A. JOHNSON, JR.
HAROLD E. THOMAS
BY
Townsend and Townsend
ATTORNEYS United States Patent Office Plant Pat. 2,892
Patented June 10, 1969

2,892
STRAWBERRY PLANT

Harold A Johnson, Jr., and Harold E. Thomas, Morgan Hill, Calif., assignors to Driscoll Strawberry Associates, Morgan Hill, Calif., a corporation of California Filed July 10, 1967, Ser. No. 652,378
Int. Cl. A01h 5/08
U.S. Cl. Plt.—48 1 Claim This invention relates to a new and distinct variety of strawberry plant which is the result of a cross of the unpatented spring producing variety known as The Strawberry Institute of California selection No. C72.26 with the subject of United States Plant Patent No. 1,735, Goldsmith et al., issued July 29, 1958. The C72.26 selection is derived from a cross of the University of California varieties known as Cal. 677.10 and Cal. 752.46.

The seedlings resulting from the aforementioned cross were grown and asexually multiplied in Tehama County, Calif.; and tested in the fruiting beds of The Strawberry Institute's selection and testing grounds at San Martin, Calif. Clones of these seedlings were also held at The Strawberry Institute's Propagation Nursery in Shasta, County. One plant was selected from the aforementioned group of seedlings, and further asexual reproduction was performed in the Shasta County nursery of the institute. Tests followed in various parts of California during intervening seasons on various institute members' properties. These tests indicated the merit of this new plant and resulted in its selection as a promising test variety.

A plant of the new variety typical in size, shape, and color is pictured in the accompanying drawing in which one ripe berry is shown indicating the typical shape during late May and June. A second berry is shown in cross section to exemplify flesh color and core cavity. The inflorescence pictured is typical of branching and relative size. The flower facing the camera is a primary, and the flower whose calyx is facing the camera is a secondary.

A distinguishing characteristic of this new plant is that it is a small, compact plant the first growing year, usually becoming strong but still open the second growing year. It may remain smaller both first and second years unless it is given excessive nutrients and water. The plant is similar to the Goldsmith, United States Patent No. 1,735 in size, appearance and color, but during the second growing year the new variety does not produce leaves that purple during the late summer months as does the Goldsmith and, thus, the plant remains lighter in color.

Another characteristic distinguishing this new variety when winter planted, is the crown crop which comes from the flowers initiated in the crown while the plant is still growing at the nursery. This crop produces many large, well formed conic berries that are usually longer than wide. This crop is normally larger and of better appearance than what the Goldsmith produces. Subsequent crops, the first growing year, are more globular in shape and are wider than they are long. If both this and the Goldsmith varieties are planted during the winter with equal chilling, the Goldsmith is the more dependable summer producer of the two during the first growing year.

During the second growing year the production pattern, fruit size and appearance is quite similar to Goldsmith. The fruit shape of the new variety is still more globular than the Goldsmith, but it is equal in skin and flesh firmness. This firmness which is reflected in its ability to ship to distant markets and remain in good condition, is one of this new variety's most outstanding attributes.

If this new variety is planted during the summer, the spring crop that follows is quite early. Coming so early (March in the Watsonville area) that much of the fruit may be malformed due to improper flower fertilization. Even normally pollenated fruit coming early after a summer planting may have longitudinal furrows on many berries, but they usually remain large and glossy and do not distract from the over-all appearance of the fruit.

The new variety of this invention is a superior pollen producer to the Goldsmith. Calyx of the new invention is generally smaller in diameter than the Goldsmith, with narrower sepals, but the apex of the sepals of the new invention are more serrated.

The leaves of the new invention during the second growing year are generally equal to the Goldsmith in overall size, but the petioles of the new varieties are more apt to have bracts present. (See drawing photograph.) The size of the central leaflet is usually equal to or larger than the Goldsmith, with the width mostly equal to the length. The serrations on the margins of the leaflets are often double-pointed in contrast to the Goldsmith which usually has a single point at each serration. Recently matured leaflets have less pubescence on their upper side, are less rugose and are glossier than the Goldsmith. The leaflets of the new invention are less rigid and tend to be more pliable than the Goldsmith.

This new variety produces fewer runners at the nursery than the Goldsmith variety.

In comparison with the Goldsmith variety the dessert quality is usually considered superior, with a mild subacid flavor. There is generally no particular aroma peculiar to the flesh of this new variety.

The new variety of this invention has a relatively high level of verticillium wilt resistance, but is susceptible to the red stele disease. As a seedling this variety withstood the natural virus invasion of the virus components found in the Santa Clara Valley without losing its ability to produce. The invention is tolerant to powdery mildew, but is susceptible to two-spotted mite.

The varietal characteristics of this new plant, described below in detail, were observed during the first and second fruiting years following a winter planting. Observations were made in the Watsonville and Salinas areas of California which are cool coastal areas near the Pacific Ocean. The color terminology is in accordance with Ridgway's Color Standards and Nomenclature (1912 edition).

*Plant.*—Medium size, open, and extensive root system.

*Leaves.*—Medium to large size. The central leaflet diameter is mostly 7 to 8 cm. with the length usually equal to the width. Leaflets are only slightly rugose, noticeably pliable, with the surface glossy and only slightly pubescent. Petioles are medium to long in length with bracts often present. Serrations at leaflet margins ovate with an acute apex becoming double pointed at times. The leaflet upper-side color during July is Forest Green, Plate XVII.

*Runners.*—Vigorous; with only a few produced in the fruiting beds. Nursery production of plants is considered low to medium.

*Inflorescence.*—Medium to long, mostly 15 to 25 cm. in length. Many pedicels producing primary berries originate from peduncles, but some may originate from the axil formed by the union of peduncles (see drawing photograph—the pedicel here originates from the peduncle near the axil). Flowers may be visible above the foliage.

*Fruit.*—Large; dropping in size during the season. Primary berries produced from the crown crop of first year producing winter planted plants reach 40 to 45 mm. in length and are conic in shape, as described by the USDA Bulletin 1043, with the length greater than the width. The subsequent main crop is globose to globose-wedge, with the width greater than the length. The apex of the fruit during this summer crop often becomes seedy, folded and not colored uniformly. The fruit during the second fruiting year is usually globose-wedge in shape, with the apex not as prone to become folded and seedy. The shoulders of most berries are large, round, not necked. The fruit surface is mostly smooth and firm with a high gloss.

Surface color varies from Strawberry Pink, Plate I, to Scarlet, Plate I. The inside is mostly Nopal Red, Plate I.

*Seeds.*—Abundant and evenly spaced, medium size with very few which are non-fertile. The seeds are usually held equal to, to above the fruit surface. Seed color is Apricot Yellow, Plate IV, becoming dark when exposed to full sunlight.

*Calyx.*—Medium to large; the calyx of most primaries is 32 to 33 mm. in diameter, and usually joins the pedicel at a point sunken within the fruit outline if the berry is viewed from the side, giving the calyx a reflexed appearance (see drawing photograph). The sepals are abundant, and mostly narrow with only a slight overlapping of each other. Serrations are often present at the apex of sepals from primary berries. The calyx is capped with difficulty. The color of sepals on the side facing the fruit is Cedar Green, Plate VI.

We claim:

1. The new and distinct variety of strawberry plant herein described and illustrated, and identified by the characteristics enumerated above.

No references cited.

ROBERT E. BAGWILL, *Primary Examiner.*